(12) United States Patent
Ko et al.

(10) Patent No.: US 10,001,444 B2
(45) Date of Patent: Jun. 19, 2018

(54) SURFACE INSPECTING METHOD

(71) Applicant: Samsung Electronics Co., Ltd., Suwon-si, Gyeonggi-do (KR)

(72) Inventors: Kang-woong Ko, Seoul (KR); Sung-yoon Ryu, Suwon-si (KR); Young-hoon Sohn, Incheon (KR); Gil-woo Song, Hwaseong-si (KR); Tae-heung Ahn, Seoul (KR); Hyoung-jo Jeon, Suwon-si (KR); Sang-kyeong Han, Seongnam-si (KR); Masahiro Horie, Suwon-si (KR); Woo-seok Ko, Seoul (KR); Yu-sin Yang, Seoul (KR); Sang-kil Lee, Yongin-si (KR); Byeong-hwan Jeon, Yongin-si (KR)

(73) Assignee: Samsung Electronics Co., Ltd. (KR)

( * ) Notice: Subject to any disclaimer, the term of this patent is extended or adjusted under 35 U.S.C. 154(b) by 260 days.

(21) Appl. No.: 14/955,635

(22) Filed: Dec. 1, 2015

(65) Prior Publication Data

US 2016/0153915 A1 Jun. 2, 2016

(30) Foreign Application Priority Data

Dec. 2, 2014 (KR) .................. 10-2014-0170833

(51) Int. Cl.
*G01N 21/88* (2006.01)
*G01J 4/00* (2006.01)
(Continued)

(52) U.S. Cl.
CPC ............ *G01N 21/8806* (2013.01); *G01J 4/00* (2013.01); *G01N 21/21* (2013.01); *G01N 21/211* (2013.01);
(Continued)

(58) Field of Classification Search
CPC .. G01N 21/21; G01N 21/211; G01N 21/8803; G01N 21/806; G01N 21/8851; G01N 21/9501; G01N 21/956; G01N 21/95607; G01N 21/95684; G01N 21/95692; G01N 2021/213; G01N 2021/8816; G01N 2021/8835; G01N 2021/8845; G01N 2021/8848;
(Continued)

(56) References Cited

U.S. PATENT DOCUMENTS 5,907,405 A 5/1999 Mizutani et al.
5,936,734 A * 8/1999 Johs ..................... G01N 21/211
356/364
(Continued)

FOREIGN PATENT DOCUMENTS

JP 2007-048836 2/2007
KR 10-0815959 3/2008

*Primary Examiner* — Gordon J Stock, Jr.
(74) *Attorney, Agent, or Firm* — Myers Bigel, P.A.

(57) ABSTRACT

A surface inspecting method includes: irradiating an incident light beam of a first polarized state on a target object, the incident light beam comprising parallel light and having a cross-sectional area: measuring a second polarized state of a reflected light beam reflected from the target object; and performing inspection on an entire area of the target object on which the incident light beam is irradiated, based on a variation between the first polarized state and the second polarized state.

19 Claims, 11 Drawing Sheets

(51) Int. Cl.
*G01N 21/21* (2006.01)
*G01N 21/956* (2006.01)
*G01N 21/95* (2006.01)

(52) U.S. Cl.
CPC ....... *G01N 21/9501* (2013.01); *G01N 21/956* (2013.01); *G01J 2004/001* (2013.01); *G01N 2021/213* (2013.01); *G01N 2021/8848* (2013.01)

(58) Field of Classification Search
CPC ... G01N 2021/8861; G01N 2021/8864; G01N 2021/8867; G01N 2021/887; G01N 2021/8874; G01N 2021/8887; G01N 2021/8896; G01N 2021/9513; G01N 2021/95676; G01J 4/00; G01J 4/02; G01J 4/04; G01J 2004/001; G01J 2004/002; G01J 2004/004; G01J 2004/005; G01J 2004/007
See application file for complete search history.

(56) References Cited

U.S. PATENT DOCUMENTS

| | | | |
|---|---|---|---|
| 6,590,656 B2 | 7/2003 | Xu et al. | |
| 6,633,831 B2 | 10/2003 | Nikoonahad et al. | |
| 6,673,637 B2 | 1/2004 | Wack et al. | |
| 6,782,337 B2 | 8/2004 | Wack et al. | |
| 6,806,951 B2 | 10/2004 | Wack et al. | |
| 6,818,459 B2 | 11/2004 | Wack et al. | |
| 6,891,610 B2 | 5/2005 | Nikoonahad et al. | |
| 6,891,627 B1 | 5/2005 | Levy et al. | |
| 6,900,900 B2 | 5/2005 | McMillen et al. | |
| 6,917,419 B2 | 7/2005 | Fielden et al. | |
| 6,919,957 B2 | 7/2005 | Nikoonahad et al. | |
| 6,999,180 B1 | 2/2006 | Janik et al. | |
| 7,006,235 B2 | 2/2006 | Levy et al. | |
| 7,075,650 B1* | 7/2006 | Johs | G01N 21/211 356/369 |
| 7,106,425 B1 | 9/2006 | Bultman et al. | |
| 7,130,029 B2 | 10/2006 | Wack et al. | |
| 7,151,609 B2 | 12/2006 | Chalmers et al. | |
| 7,280,212 B2 | 10/2007 | Mieher et al. | |
| 7,301,649 B2 | 11/2007 | Fabrikant et al. | |
| 7,307,724 B1* | 12/2007 | Liphardt | G01N 21/211 356/369 |
| 7,321,426 B1 | 1/2008 | Poslavsky et al. | |
| 7,323,681 B1* | 1/2008 | Oldham | G01N 21/6428 250/208.1 |
| 7,511,828 B2 | 3/2009 | Watanabe et al. | |
| 7,580,065 B2* | 8/2009 | Shimizu | G06T 3/4069 348/207.99 |
| 7,616,313 B2 | 11/2009 | Kandel et al. | |
| 7,733,502 B2 | 6/2010 | Moriya et al. | |
| 8,179,530 B2 | 5/2012 | Levy et al. | |
| 8,304,724 B2 | 11/2012 | Sasajima et al. | |
| 8,619,235 B2 | 12/2013 | Van Drent | |
| 8,634,069 B2 | 1/2014 | Nakano et al. | |
| 2011/0115793 A1* | 5/2011 | Grycewicz | G06T 3/4069 345/428 |
| 2013/0114085 A1* | 5/2013 | Wang | G01N 21/55 356/445 |
| 2014/0152804 A1* | 6/2014 | Ahner | G06T 7/0004 348/92 |

* cited by examiner

SURFACE INSPECTING METHOD

CROSS-REFERENCE TO RELATED APPLICATION

This application claims priority to Korean Patent Application No. 10-2014-0170833, filed on Dec. 2, 2014, the disclosure of which is incorporated herein by reference in its entirety.

BACKGROUND

The inventive concept relates to a surface inspecting method, and more particularly, a surface inspecting method using an optical method.

In manufacturing semiconductor elements, patterns designed for each manufacturing process may need to be accurately formed in the semiconductor elements. In order to inspect the patterns, shapes of the semiconductor elements are optically observed, but it may be difficult to accurately analyze nanoscale patterns due to low resolutions.

In order to solve the low resolutions, specific shapes are analyzed using an electron microscope. However, when using the electron microscope, the semiconductor elements are cut into cross-sections and the measurements are performed in a vacuum state. Thus, an inspection rate is slow and it is difficult to select various measurement regions.

SUMMARY

The inventive concept provides a surface inspecting method, capable of inspecting an entire surface of a target object and improving an inspection rate.

According to an aspect of the inventive concept, there is provided a surface inspecting method including: irradiating an incident light beam of a first polarized state on a target object, the incident light beam comprising parallel light and having a cross-sectional area; measuring a second polarized state of a reflected light beam reflected from the target object; and performing an inspection on an entire area of the target object on which the incident light beam is irradiated, based on a variation between the first polarized state and the second polarized state.

The target object may include a pattern, and the performing of the inspection may include: calculating physical quantities of an imaginary thin film indicating a same polarized state as the second polarized state with respect to the incident light beam; and calculating physical quantities of the target object from the physical quantities of the imaginary thin film by using a relationship in which a height of the pattern is proportional to a thickness of the imaginary thin film and a width of the pattern is proportional to a value acquired by dividing a material mixing ratio of the imaginary thin film by the height of the pattern.

The calculating of the physical quantities of the imaginary thin film may include: providing a theoretical model having substantially a same shape as the imaginary thin film and comparing a theoretical result of the theoretical model with a result measured with respect to the target object; adjusting a parameter of the theoretical model and acquiring a condition in which the theoretical result matches the measured result; and calculating the physical quantities of the imaginary thin film using the condition.

The surface inspecting method may further include outputting, in an image form, a difference between a theoretical spectrum indicating a theoretical result with respect to a plurality of wavelength ranges of the theoretical model and a measurement spectrum indicting a result measured with respect to the plurality of wavelength ranges in the target object; and detecting defects of the target object.

The target object may include a plurality of patterns that are periodically formed.

The measuring of the second polarized state may include: irradiating a plurality of light beams having different wavelength ranges on the target object in time series; and measuring a plurality of light beams reflected from the target object in time series.

The surface inspecting method may be performed with respect to each of a plurality of wavelength ranges, and the surface inspecting method further comprises outputting, in an image form, a polarization spectrum indicating each second polarized states according to the plurality of wavelength ranges after the inspection.

The performing of the inspection may include: providing a theoretical model having substantially a same shape as the target object and comparing a theoretical result of the theoretical model with respect to a polarized state and a result measured with respect to the target object; adjusting a parameter of the theoretical model such that the theoretical result matches the measured result; and irradiating incident light beams having various incidence angles on the theoretical model and the target object and calculating the flatness of the surface of the target object according to a difference between polarized states of reflected light beams reflected from the theoretical model and the target object.

The performing of the inspection may include: dividing a polarization spectrum for each element region with respect to the target object by using a designed pattern of the target object; and measuring a specific defect tendency for each element region from a distribution tendency of the polarization spectrum divided for each element region.

The measuring may be performed by a detector, and a sub-pixel means that a pixel region capable of being maximally resolved by the detector is divided into at least two regions, and the surface inspecting method may further include, after the inspection, moving a stage supporting the target object by the sub-pixel.

According to another aspect of the inventive concept, there is provided a surface inspecting method includes: irradiating an incident light beam of a first polarized state on a first inspection region, and primarily measuring a second polarized state of a reflected light beam reflected from the first inspection region; moving a stage supporting a target object by a sub-pixel such that the incident light beam is irradiated on a second inspection region overlapping the first inspection region by an area of at least one sub-pixel; and irradiating an incident light beam of a third polarized state on the second inspection region, and secondarily measuring a fourth polarized state of a reflected light beam reflected from the second inspection region, wherein a sub-pixel is smaller than a pixel region, and a pixel region is a region that is capable of being maximally resolved by a detector.

The incident light beam may be a parallel light beam having a cross-sectional area, and the incident light beam may be irradiated on the entire first inspection region in the primarily measuring and may be irradiated on the entire second inspection region in the secondarily measuring.

The surface inspecting method may further include synthesizing overlapped regions of a first image of the second polarized state with respect to the first inspection region and a second image of the third polarized state with respect to the second inspection region.

The moving and the secondarily measuring may be repeated twice or more.

The stage may be movable in at least one of a vertical direction and a horizontal direction by at least one sub-pixel.

According to an aspect of the inventive concept, a surface inspecting method includes irradiating an incident light beam of a first polarized state on a first inspection region, and primarily measuring a second polarized state of a reflected light beam reflected from the first inspection region with a detector; and irradiating an incident light beam of a third polarized state on a second inspection region, and secondarily measuring a fourth polarized state of a reflected light beam reflected from the second inspection region with the detector. The second inspection region is offset from the first inspection region by less than a pixel of the detector, and the pixel of the detector is a region that is capable of being maximally resolved by a detector.

The first and second inspection regions may be offset by moving a stage supporting a target object by a sub-pixel such that the incident light beam is irradiated on a second inspection region overlapping the first inspection region by an area of at least one sub-pixel.

The incident light beam may be a parallel light beam having a cross-sectional area, and the incident light beam may be irradiated on the entire first inspection region in the primarily measuring and may be irradiated on the entire second inspection region in the secondarily measuring.

Overlapped regions of a first image of the second polarized state with respect to the first inspection region and a second image of the third polarized state with respect to the second inspection region may be synthesized.

The moving and the secondarily measuring steps may be repeated.

BRIEF DESCRIPTION OF THE DRAWINGS

Example embodiments of the inventive concept will be more clearly understood from the following detailed description taken in conjunction with the accompanying drawings in which.

DETAILED DESCRIPTION OF THE EMBODIMENTS

Figure 1:
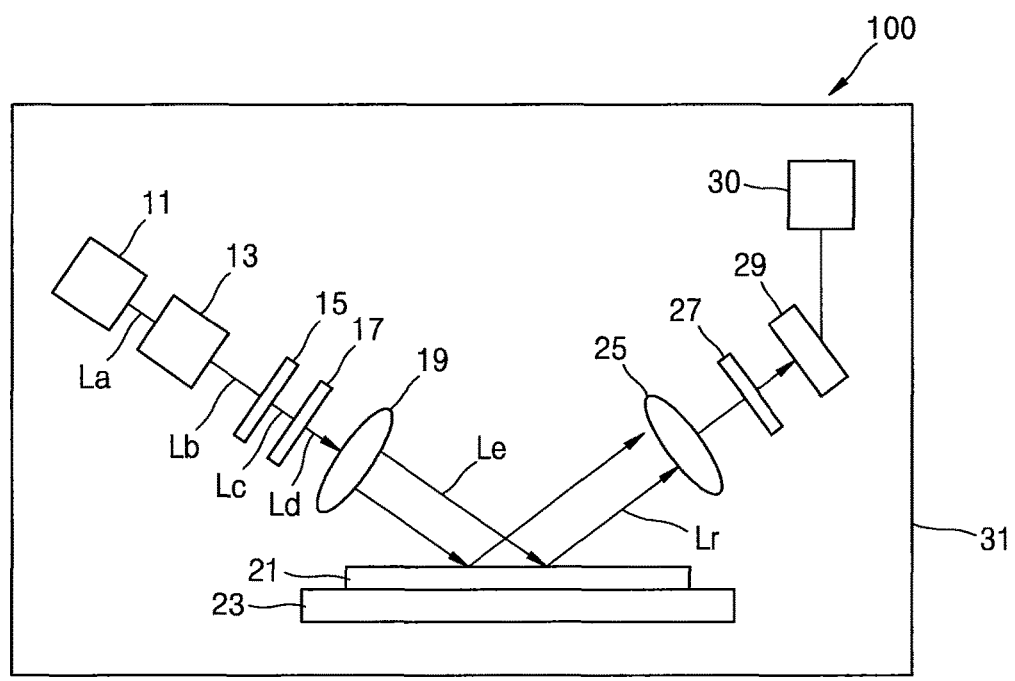
FIG. 1 is a schematic view of a surface inspecting apparatus used in a surface inspecting method according to an example embodiment of the inventive concept.

Hereinafter, embodiments of the inventive concept will be described with reference to the accompanying drawings. The inventive concept may, however, be embodied in many different forms and should not be construed as being limited to the embodiments set forth herein; rather, these embodiments are provided so that this disclosure will be thorough and complete, and will fully convey the inventive concept to those of ordinary skill in the art.

Also, though terms "first" and "second" are used to describe various members, components, regions, layers, and/or portions in various embodiments of the inventive concept, the members, components, regions, layers, and/or portions are not limited to these terms. These terms are used only to differentiate one member, component, region, layer, or portion from another one. Therefore, a member, a component, a region, a layer, or a portion referred to as a first member, a first component, a first region, a first layer, or a first portion in an embodiment may be referred to as a second member, a second component, a second region, a second layer, or a second portion in another embodiment.

Unless otherwise defined, all terms used herein, including technical and scientific terms, have the same meaning as commonly understood by one of ordinary skill in the art to which the inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In the accompanying drawings, the modifications of the illustrated shapes may be expected according to manufacturing technologies and/or tolerance. Therefore, the example embodiments should not be construed as being limited to specific shapes of the illustrated regions. The shapes may be changed during the manufacturing processes.

In the drawings, the dimensions of structures are exaggerated or reduced for clarity of the inventive concept.

FIG. 1 is a schematic view of a surface inspecting apparatus 100 used in a surface inspecting method according to an example embodiment of the inventive concept.

Referring to FIG. 1, the surface inspecting apparatus 100 may include a light source 11 configured to emit a light beam La, a monochrometer 13 configured to transmit a light beam Lb in a specific wavelength range of the light beam La, a polarizer 15 configured to transmit a light beam Lc having a specific polarization direction of the light beam Lb, a compensator 17 configured to delay a phase of a P wave of the light beam Lc, a collimating lens 19 configured to collimate the phase-delayed light beam Ld into a parallel light beam Le, a stage 23 configured to support a target object 21 on which the parallel light beam Le is irradiated, a condensing lens 25 configured to condense a light beam Lr reflected from the target object, an analyzer 27 configured to analyze a polarization direction of the light beam Lr, a detector 29 configured to detect image information from the reflected light beam Lr, and a processor 30 configured to acquire at least one characteristic of the target object 21 by using a variation in the polarization direction. The surface inspecting apparatus 100 may be disposed inside a chamber 31 maintaining a constant temperature therein. As used herein, a "parallel" light beam refers to a light beam that has been collimated, such as by a collimating lens.

The light source 11 may be a point light source. When the light beam La is diffused and emitted by the point light source, the light beam La may be collimated into the parallel light beam Le by the collimating lens 19. The light source 11 may be a white light source, but is not limited thereto. Any suitable light source may be used, and the light source 11 may include a light source having at least one wavelength from a range of wavelengths.

The monochrometer 13 may select a specific wavelength range of the light beam La emitted from the light source 11. That is, the light beam La may be adjusted to have a first wavelength range λ1 through the monochrometer 13.

In addition, light beams having different wavelength ranges λ1, λ2, λ3, . . . , λn may be irradiated on the target object 21 in time series and light beams Lr reflected from the target object 21 may be adjusted for a time-series measurement. After measuring by using the light beam La having the first wavelength range λ1 is completed, measurements by using the light beam Lb having second, third, . . . nth wavelengths λ2, λ3, . . . , λn that are different from the first wavelength range λ1 may be performed by adjusting the monochrometer 13. That is, the target object 21 may be measured with respect to the plurality of wavelength ranges λ1, λ2, λ3, . . . , λn. A more accurate inspection may be performed by measuring the target object 21 with respect to the plurality of wavelength ranges λ1, λ2, λ3, . . . , λn.

The polarizer 15 may arbitrarily determine a polarized state of the light beam Lc. The polarizer 15 may adjust the polarized state of the light beam Lc such that the light quantity irradiated on the target object 21 is sufficiently secured. At this time, an optimal polarization direction may be selected so as to transmit a sufficient light quantity according to a wavelength range. Therefore, the polarization direction of the polarizer 15 may be arbitrarily adjusted according to the wavelength range of the light beam Lb incident on the polarizer 15. Accordingly, the light beam Lc emitted through the polarizer 15 may maintain a constant level of light quantity. The polarizer 15 may be adjusted in a first polarization direction with respect to the light beam La having the first wavelength range λ1 emitted through the monochrometer 13 and may be adjusted in a second direction with respect to the light beam Lb having the second wavelength range λ2.

The compensator 17 delays a phase of a P wave of the light beam Lc passing through the polarizer 15. The light beam Lc has a specific polarized state and may be separated into an S wave and a P wave, and the light beam Ld may be adjusted to a circularly polarized state by delaying the phase of the P wave of the light beam Lc by 90°. The circularly polarized state allows a variation in the polarized state on the target object 21 to be more easily measured. The compensator 17 may be rotated to adjust a degree of a phase delay of the light beam Lc. In some example embodiments, a phase modulator may be used instead of the compensator 17. The phase modulator may adjust the phase of the light beam Lc like the compensator 17. In some embodiments, the compensator 17 may be omitted.

The collimating lens 19 may collimate the light beam Ld into the parallel light beam Le. Accordingly, the cross-section of the light beam Le has a predetermined area, and the light beam Le is irradiated on a relatively wide area of the target object 21.

According to a general inspecting method, the light beam irradiated on the target object 21 is collected so as to be irradiated on an arbitrary spot of the target object 21. The collected light beam monitors the arbitrary spot of the target object 21. In order to monitor a plurality of spots of the target object 21, measurements may be repeatedly performed by moving an illumination unit including the stage 23, the light source 11, or the like. Accordingly, in order to inspect the entire area of the target object 21, excess time may be taken. In addition, in a calculating process of grasping real characteristics of the target object 21, a lot of measured values with respect to the plurality of spots may be needed. Thus, calculation load may be increased and the calculation is difficult.

However, in the surface measuring method according to the example embodiment of the inventive concept, the collected light beam is not irradiated on each spot of the surface of the target object 21. The light beam Le having a predetermined area is irradiated on the target object 21 and the reflected light beam Lr is detected. Thus, the plurality of spots of the target object 21 may be measured at the same time. Accordingly, inspection time may be effectively reduced.

The target object 21 of the surface inspecting apparatus 100 may be a semiconductor element including a thin film or a periodic structure, or various objects during the manufacturing of a semiconductor element. The surface inspecting apparatus 100 irradiates the polarized light beam on the target object 21 in the form of the parallel light beam Le. In the light beam Le irradiated on the target object 21, an S wave is totally reflected from the target object 21, and a P wave transmits through the target object 21 or is reflected from a material interface in the target object 21. At this time, the phase and amplitude of the P wave vary. Thus, after the interference with the S wave, the P wave has a varying polarized state. The P wave may have a variety of elliptically polarized states according to a phase difference between the S wave and the P wave. A dimension of the polarized state may be acquired by the detector 29. In addition, a polarization spectrum according to a wavelength, that is, a spectrum having Ψ and Δ values may be acquired through a Jones matrix, a stroke vector, or a Miller matrix. The psi (Ψ) value denotes a reflection coefficient ratio or a phase width of the P wave and the S wave, and the delta (Δ) value denotes a phase difference between the P wave and the S wave. Since all polarized states may be denoted by the Ψ and Δ values, the variation in the polarized state may be measured according to the variations in the Ψ and Δ values.

The stage 23 supports the target object 21 and may be vertically and horizontally moved to a measurement region of the target object 21. The stage 23 may be moved by a sub-pixel distance as defined by the detector 29. The sub-pixel or sub-pixel distance means that a pixel unit capable of being maximally resolved by the detector 29 is divided into regions that are smaller than the pixel unit. Accordingly, the surface inspecting apparatus 100 may acquire first image information on a first inspection region and acquire second to nth image information on second to nth inspection regions moved by a sub-pixel distance from a region surrounding the first inspection region. The first to nth image information may be synthesized into one piece of information at a mutually overlapped location, and accordingly, the stage 23 may have higher spatial resolution power than the detector 29. This will be described below.

The condensing lens 25 may condense the parallel light beam Lr reflected from the target object 21.

The analyser 27 measures a polarized state of the light beam Lr reflected from the target object 21. When the light beam Lc having a specific polarized state through the polarizer 15 is irradiated on and reflected from the target object 21 through the compensator 17 and the collimating lens 19, the polarized state varies according to a surface state or an inner structure of the target object 21. In this case, a variation amount of the polarized state of the light beam Le varies according to the wavelength range of the light beam Le. The light beam Lr having the varying polarized state may be detected through the condensing lens 25 and the analyser 27, and surface characteristics of the target object 21 may be measured by using the variation in the polarized state without destroying the target object 21.

The analyser 27 may be rotated and the polarization direction thereof may be selected so as to transmit only an arbitrary polarized component. In some example embodiments, a compensator may be further disposed between the target object 21 and the analyser 27. Therefore, the compensator may delay the phase of the P wave of the light beam Lr reflected from the target object 21.

The detector 29 receives the light beam Lr and converts the received light beam Lr into an electric signal. The detector 29 may include a photoelectric device such as a charge-coupled device (CCD), a complementary metal-oxide semiconductor (CMOS), or a photo multiplier tube (PMT). The detector 29 measures a variation in the polarized state of the light beam Lr according to the plurality of wavelength ranges $\lambda 1, \lambda 2, \lambda 3, \ldots \lambda n$.

The processor 30 may perform a calculation process so as to acquire at least one characteristic of the target object 21 by using a variation in the polarization direction. That is, the processor 30 may calculate at least one characteristic of the target object 21 by using polarization information, that is, $\Psi$ and $\Delta$ values.

At least one characteristic of the target object 21 may be a critical dimension (CD), a defect, a film thickness, optical properties of a film, flatness of a film, or a combination thereof. In addition, the processor 30 may calculate the above-described characteristics of the target object 21 separately or simultaneously. The physical properties of the film may include a refractive index or an absorption coefficient.

In the surface inspecting apparatus 100, the monochrometer 13, the polarizer 15, and the compensator 17 are illustrated in this order, but the inventive concept is not limited thereto. The monochrometer 13, the polarizer 15, and the compensator 17 may be disposed in any order.

Figure 2A:
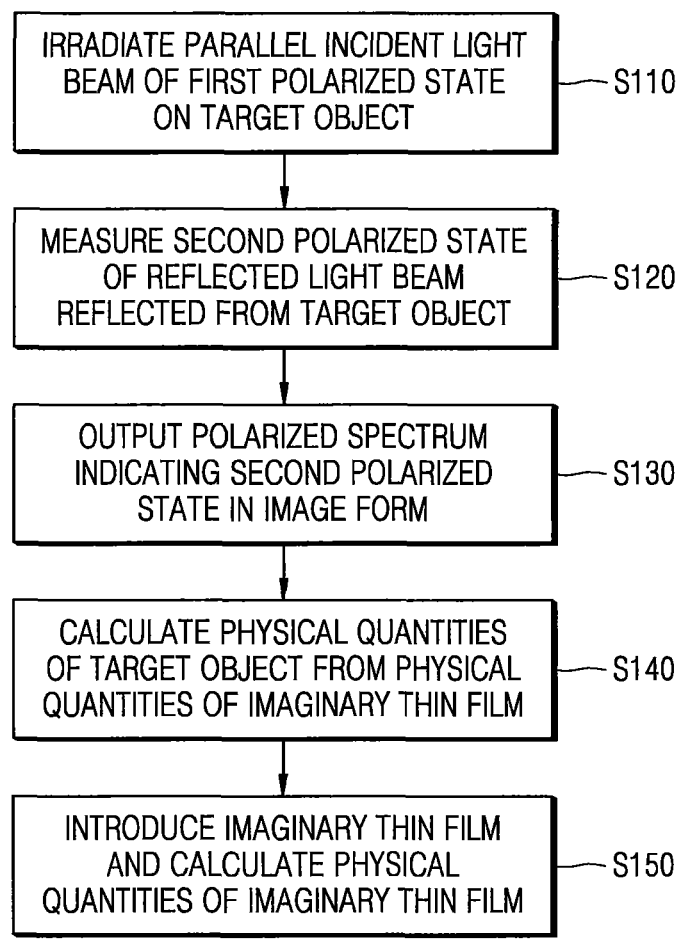
FIGS. 2A and 2B are flowcharts of a surface inspecting method according to an example embodiment of the inventive concept.
Figure 2B:
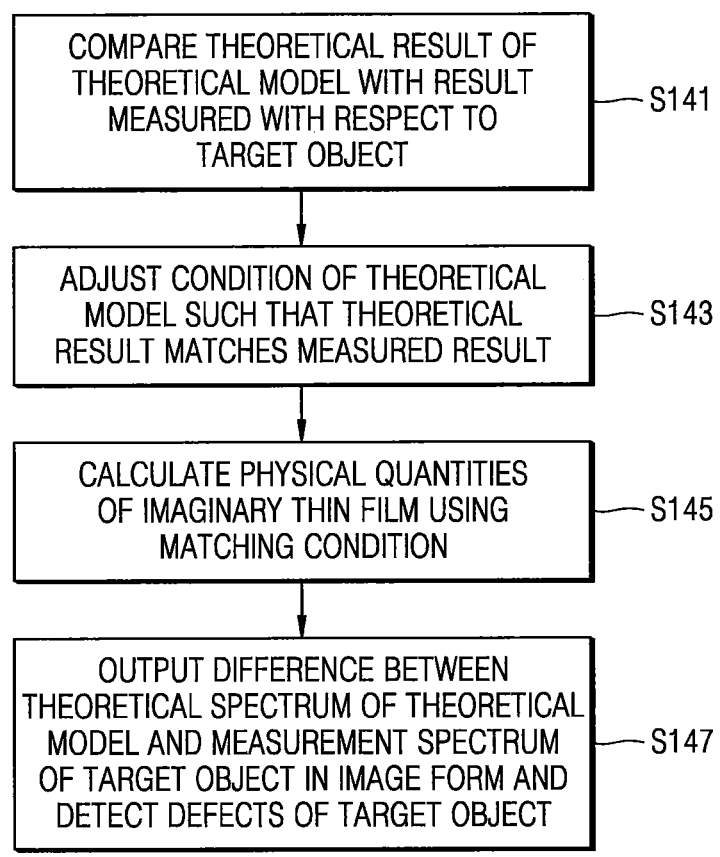

FIGS. 2A and 2B are flowcharts of a surface inspecting method according to an example embodiment of the inventive concept.

Referring to FIG. 2A, the surface inspecting method may include irradiating an incident light beam of a first polarized state on a target object 21, the incident light beam being parallel and having a cross-sectional area (S110), and measuring a second polarized state of a reflected light beam reflected from the target object 21 (S120). At this time, since the incident light beam is irradiated on the target object 21 as the parallel light beam having the cross-sectional area, the inspection on the entire area of the target object 21 on which the incident light beam is irradiated may be performed by a variation in the first polarized state and the second polarized state. The surface inspecting method is performed by using a plurality of wavelength ranges. A polarization spectrum indicating second polarized states according to the plurality of wavelength ranges may be output in an image form (S130). In some embodiments, the outputting of the image S130 may be omitted.

In a general surface measuring method, a condensed light beam is irradiated on each spot of the target object and a reflected light beam is detected. In this case, a light beam is irradiated on an entire area of the target object on a spot-to-spot basis and a reflected light beam is detected, which may take a lot of time. On the contrary, according to example embodiments of the inventive concept, a light beam is enlarged into a parallel light beam, so that the light beam is irradiated on not a specific spot but a predetermined area. When the light beam reflected from the area on which the light beam is irradiated is detected, a plurality of spots included in the area may be inspected at the same time, thereby reducing inspection time.

Even when a pattern is formed on the surface of the target object 21, a critical dimension or the like of the pattern may be easily acquired through the parallel light beam by introducing an imaginary thin film instead of the surface on which the pattern is formed, without irradiating a light beam on a spot-to-spot basis. The imaginary thin film, which indicates the same polarized state as the second polarized state with respect to the incident light beam, is introduced, and physical quantities of the imaginary thin film may be calculated (S140). Since the imaginary thin film has a flat surface, the physical quantities of the imaginary thin film may be easily calculated. After that, the physical quantities of the target object 21 may be calculated from the physical quantities of the imaginary thin film (S150). In this case, an interaction formula in which the height of the pattern is proportional to the thickness of the imaginary thin film, and the width of the pattern is proportional to the value acquired by dividing the material mixing ratio of the imaginary thin film by the height of the pattern may be used.

FIG. 2B is a flowchart of operation (S140) of calculating the physical quantities of the imaginary thin film in FIG. 2A.

Referring to FIG. 2B, a theoretical result of the theoretical model may be compared with a result measured with respect to the target object 21 by introducing a theoretical model having substantially the same shape as the imaginary thin film (S141). After that, a physical condition of the theoretical model may be adjusted such that the theoretical result matches the measured result (S143). The physical condition of the theoretical model, which is adjusted such that the theoretical result matches the measured result, is the same as that of the imaginary thin film, and other physical quantities of the imaginary thin film may be calculated (S145).

In some example embodiments, defects of the target object 21 may be detected by outputting, in an image form, a difference between a theoretical spectrum indicating the theoretical result with respect to a plurality of wavelength ranges of the theoretical model and a measurement spectrum indicating the measured result with respect to a plurality of wavelength ranges in the target object 21 (S147). Operation (S147) of detecting the defects by comparing images may be omitted.

Figure 3A:
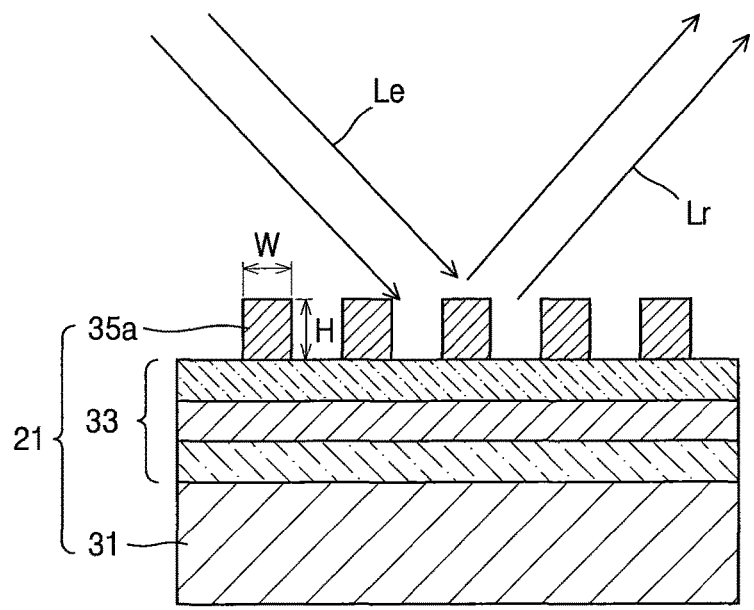
FIGS. 3A and 3B are schematic views of a case where an imaginary thin film is introduced instead of a target object in the surface inspecting method of FIG. 2A.
Figure 3B:
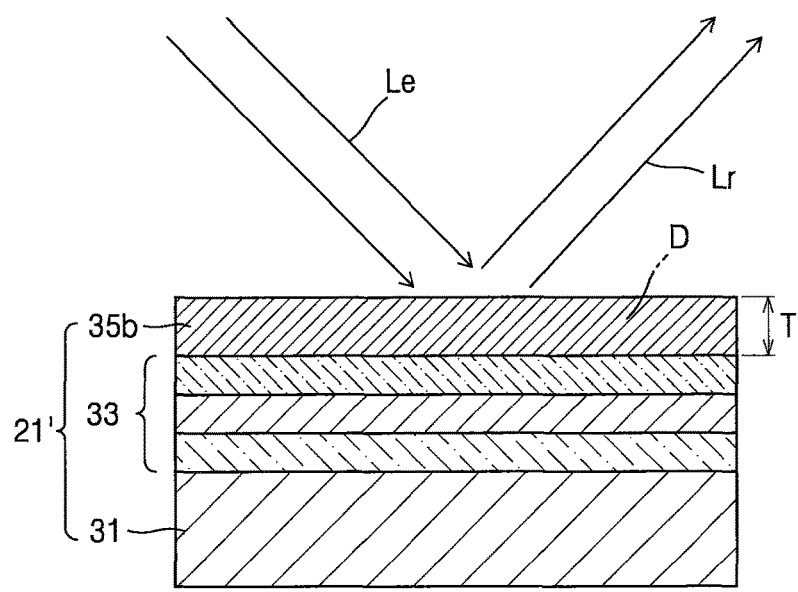

FIGS. 3A and 3B are schematic views of a case where the imaginary thin film is introduced instead of the target object 21 in the surface inspecting method of FIG. 2A.

FIG. 3A is a conceptual diagram of a real target object, and FIG. 3B is a conceptual diagram of an imaginary thin film that is assumed to be substantially the same as the real target object of FIG. 3A.

FIGS. 3A and 3B illustrate a method of measuring characteristics, especially a critical dimension, of the target object 21 having a periodic structure on a surface thereof by using the surface inspecting apparatus 100. The target object 21 includes a substrate 31, a multi-layered thin film 33, and a plurality of pattern structures 35a that are periodically formed on the multi-layered thin film 33. The pattern structures 35a may have similar structures. The pattern structures 35a have a height H and a width W and are separate from one another.

Generally, in analyzing the surface on which the pattern structures 35a is formed, since the pattern structure 35a is formed or is not formed according to each spot of the surface, a method of irradiating a light beam on a spot-to-spot basis and detecting each reflected light beam is used. Such a method has to irradiate the light beam on each spot of the target object 21 and measure Ψ and Δ values, and the Ψ and Δ values with respect to each spot are calculated through complex calculation processes such as rigorous coupled-wave analysis (RCWA) and fast track drug development (FTDD). As a result, much time may be taken.

However, according to the example embodiment of the inventive concept, in order to measure the height H and the width W of the pattern structure 35a, a flat imaginary thin film 35b (see FIG. 3B), which substantially has the same optical characteristic as the periodically formed pattern structures 35a, may be assumed. This assumption may be effective when a distance between the pattern structures 35a is less than the wavelength of the incident light beam Le.

While the multi-layered thin film 33 is illustrated as being formed between the substrate 31 and the plurality of pattern structures 35a, the inventive concept is not limited thereto. The multi-layered thin film 33 may be omitted.

In some example embodiments, the substrate 31, the multi-layered thin film 33, and the plurality of pattern structures 35a may be a part of semiconductor elements or a structure formed during the manufacturing of a semiconductor element.

Referring to FIG. 3B, since the surface of the imaginary thin film 35 has the same surface structure with respect to each spot, a method of irradiating a light beam on each spot and detecting a reflected light beam from each spot is not required. Therefore, the parallel light beam Le having a wide cross-sectional area is irradiated on the imaginary thin film 35b, and thus, Ψ and Δ values may be measured from the light beam Lr reflected from the imaginary thin film 35b. In order to measure characteristics such as a thickness T, a density D, or a refractive index n of the imaginary thin film 35b, an analysis modeling method may be used. The analysis modeling method is a process of analyzing an experimental result. As an example of the analysis modeling method, there is a method of comparing a theoretical model with an experimental model. That is, a theoretical result of the theoretical model is compared with a result measured with respect to a real model, and the real model is analyzed by correcting the theoretical model such that both of the results are matched with each other. In this manner, other characteristics of the real model may be measured.

Specifically, in order to measure characteristics such as the thickness T, the density D, or the refractive index n of the imaginary thin film 35b from the Ψ and Δ values, the theoretical model may be introduced. The theoretical model is a B material layer deposited on an upper layer of the multi-layered thin film 33 by an A thickness, and the experimental model is the imaginary thin film 35b formed on the upper layer of the multi-layered thin film 33. The theoretical model is introduced so as to know theoretical Ψ' and Δ' values, and the A thickness and the B material are known values. The theoretical model may generate the theoretical Ψ' and Δ' values under the same condition as the experimental model. In order to substantially match the theoretical Ψ' and Δ' values of the theoretical model with the Ψ and Δ values of the experimental model, the A thickness of the theoretical model and the refractive index of the B material may be adjusted. When the theoretical Ψ' and Δ' values of the theoretical model are substantially matched with the Ψ and Δ values of the experimental model by adjusting the A thickness of the theoretical model and the refractive index of the B material, the A thickness and the refractive index of the B material may be regarded as a thickness and a refractive index of the imaginary thin film 35b included in the experimental model. The method of introducing the theoretical model is exemplified as the method of measuring the thickness and the refractive index of the imaginary thin film 35b, but the inventive concept is not limited thereto.

Figure 4:
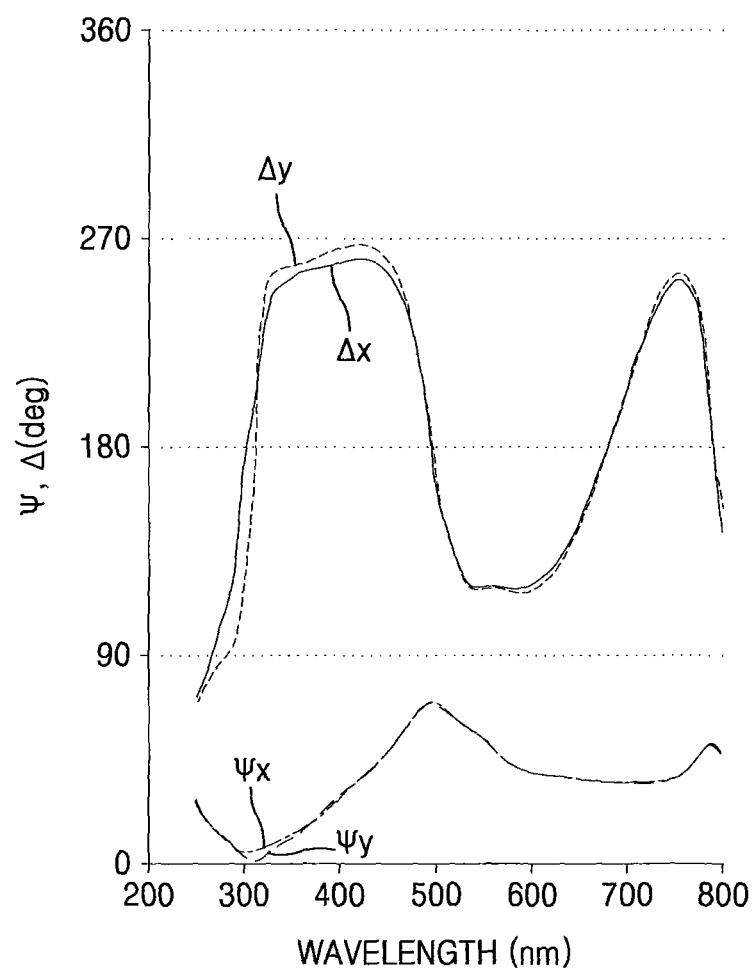
FIG. 4 is a graph of a comparison between a theoretical spectrum of a theoretical model and a measurement spectrum of a real model.

FIG. 4 is a graph of a comparison between the theoretical spectrum of the theoretical model and the measurement spectrum of the real model.

Specifically, FIG. 4 illustrates the theoretical spectrum indicating Ψx and Δx values of the theoretical model with respect to the plurality of wavelength ranges λ1, λ2, λ3, ..., λn, and the measurement spectrum indicating Ψy and αy values of the experimental model with respect to the plurality of wavelength ranges λ1, λ2, λ3, ..., λn. The Ψx and Δx values and the Ψy and Δy values are substantially matched with one another over the entire regions of the plurality of wavelength ranges λ1, λ2, λ3, ..., λn.

Referring to FIG. 3B, reflectivity characteristics of the light beam Le with respect to the imaginary thin film 35b may be acquired by using Fresnel equations. The reflectivity of the imaginary thin film 35b may be regarded as reflectivity of a layer on which the plurality of pattern structures 35a of FIG. 3A having the same optical characteristics as the imaginary thin films 35b are formed. According to the surface inspecting method according to the example embodiment of the inventive concept, the reflectivity of the target object 21 may be easily measured without performing a calculating process on all spots of the target object 21. In addition to the measuring of the reflectivity of the target object 21, specific shapes of the plurality of pattern structures 35a of FIG. 3A may be measured by using the imaginary thin film 35b.

In some example embodiment, defects of the target object 21 may be detected by comparing the theoretical spectrum indicating Ψ' and Δ'Ψx values of the theoretical model with respect to the plurality of wavelength ranges λ1, λ2, λ3, ..., λn with the measurement spectrum indicating Ψ and Δ values of the experimental model with respect to the plurality of wavelength ranges λ1, λ2, λ3, ..., λn. The defects of the target object 21 may greatly appear on the spectrum as it goes from an infrared range to an ultraviolet range. Therefore, a difference between the theoretical spectrum and the measurement spectrum is output as image information for each wavelength range, thereby enabling defect detection. The image information may be displayed on a display screen.

In some example embodiments, a gradient distribution of the target object 21 may be measured from a variation in the polarization spectrum. The polarization spectrum indicates Ψ and Δ values acquired with respect to the plurality of wavelength ranges λ1, λ2, λ3, ..., λn through the detector 29. Specifically, when the surface of the target object 21 is inclined by θ, an incidence angle is inclined by 2θ, so that a reflected polarization spectrum varies. Therefore, the incidence angle of the light beam used in the theoretical model is regarded as an unknown parameter and flatness distribution may be acquired by measuring an incidence angle distribution that is suitable for the polarization spectrum.

In some example embodiments, the polarization spectrum is divided for each element region by using the designed pattern of the target object, and characteristics for each element region may be measured from a distribution tendency of the divided spectrum. Therefore, the influence from the manufacturing process may be estimated by grasping a specific defect tendency for each element region. In this case, since the measuring of the characteristics for each element region includes a very complex calculation process, the measurement of the characteristics for each element region may be performed on the assumption that a plurality of patterns included in each element region have a central value. That is, even though characteristics of the plurality of the patterns are distributed within a predetermined range, the measurement of the characteristics for each element region may be performed on the assumption that plurality of patterns have the central value in the predetermined range. After that, when a result with respect to the element region is measured, fine adjustment may be performed on the plurality of patterns by setting the result as an initial value. Alternatively, a correction may be performed on the plurality of patterns by a statistical method by taking into account a variation from the central value. Due to this method, the characteristics may be more easily measured from each element region.

In some example embodiments, the images of a reference spectrum are compared with a polarization spectrum measured with respect to the real target object, and the defects may be detected according to a difference therebetween. The reference spectrum may be a defect-free polarization spectrum acquired from the target object with respect to the plurality of wavelength ranges $\lambda 1, \lambda 2, \lambda 3, \ldots, \lambda n$ or a spectrum calculated by using the designed pattern of the target object 21.

In some example embodiments, in the surface inspecting method according to the example embodiment, it may be determined whether the process is appropriately performed through an image variation in the polarization spectrum before and after a process of a processing device.

Figure 5:
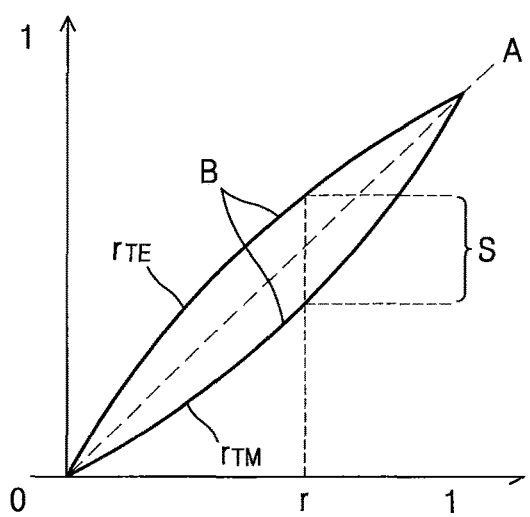
FIG. 5 is a graph of a material mixing ratio and a polarization component mixing ratio of the imaginary thin film of FIG. 3B.

FIG. 5 is a graph of a material mixing ratio and a polarization component mixing ratio of the imaginary thin film 35b of FIG. 3B.

Referring to FIG. 5, it may be assumed that the imaginary thin film 35b includes two materials mixed in a mixing ratio of r ($0 \leq r \leq 1$). In this assumption, the plurality of pattern structures 35a, which are the premise of the imaginary thin film 35b, and a space between the pattern structures 35a are regarded as a mixture of two materials. Therefore, the mixing ratio r may be regarded as a fill factor.

The mixing ratio may be divided into polarization component mixing ratios $r_{TE}$ and $r_{TM}$ according to polarization or non-polarization of the imaginary thin film 35b. The polarization or non-polarization of the imaginary thin film 35b may be determined according to whether optical characteristics of light beams incident in a direction perpendicular to one another are different from one another. That is, since the imaginary thin film 35b is isotropic and the polarization is "0", the mixture ratios $r_{TE}$ and $r_{TM}$ are equal to each other in a ratio of 1:1 along line A. For example, when the mixing ratio r of the two materials is "0" or "1", the imaginary thin film 35b does not exist or is formed of one material. Thus, the polarization is "0" and the mixture ratios $r_{TE}$ or $r_{TM}$ is either "0" or "1." However, since the imaginary thin film 35b is anisotropic and thus there is polarization, the mixing ratio $r_{TE}$ differs from the mixture ratio $r_{TM}$ along line B. A difference between the $r_{TE}$ and the $r_{TM}$ may mean anisotropic strength S. The anisotropic strength S depends on a geometric structure of the plurality of pattern structures 35a of FIG. 3A.

The mixture ratios $r_{TE}$ and the $r_{TM}$ may be acquired through a measurement, and the mixing ratio r may be acquired by using the measured mixture ratios $r_{TE}$ and $r_{TM}$ values and the following Formulas (1) and (2):

$$r_{TE} = r + S \cdot \sin \pi \cdot r \quad (1)$$

$$r_{TM} = r - S \cdot \sin \pi \cdot r \quad (2)$$

Also, as described above, the thickness and refractive index of the imaginary thin film 35b may be measured by using the analysis modeling. On the other hand, the refractive index of the imaginary thin film 35b may be acquired by using the mixing ratios $r_{TE}$ and $r_{TM}$ through the above-described analysis modeling.

Characteristics of the pattern structures 35a that are the real target object 21 may be determined from the mixing ratio r, the thickness T, the height H, and the refractive index of the imaginary thin film 35b. That is, the thickness T and the mixing ratio r of the imaginary thin film 35b has the following relationship with the height H and width W of the pattern structures 35a that are the real target object 21:

$$H \propto T \quad (3)$$

$$W \propto \frac{r}{H} \quad (4)$$

The thickness T and the mixing ratio of the imaginary thin film 35b may be known by introducing the imaginary thin film 35b without complex calculation processes. In addition, the height H and the width W of the pattern structure 35a may be easily measured from the thickness T and the mixing ratio r of the imaginary thin film 35b.

In some example embodiments, the pattern structure 35a may be an object formed during the semiconductor manufacturing process. Therefore, the surface inspecting method according to the example embodiment of the inventive concept may measure a height and a width of a structure included in a semiconductor element.

Figure 6:
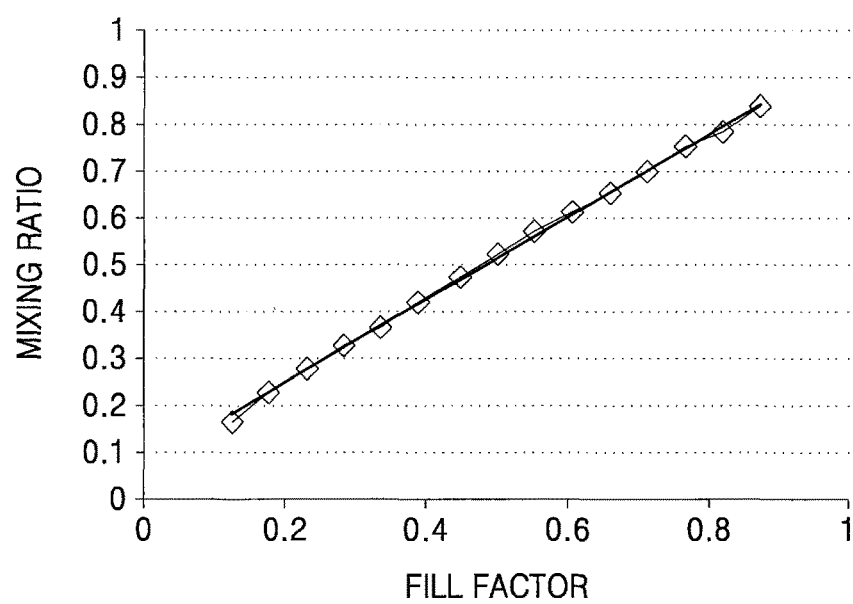
FIG. 6 is a graph of a fill factor of a real target object and a material mixing ratio of an imaginary thin film, which are acquired by the surface inspecting method according to the example embodiment of the inventive concept.

FIG. 6 is a graph of a fill factor of a real target object and a material mixing ratio of an imaginary thin film, which are acquired by the surface inspecting method according to the example embodiment of the inventive concept.

Referring to FIG. 6, the fill factors of the plurality of pattern structures 35a of FIG. 3, which are the real target object 21, and the space therebetween, and the mixing ratio of the imaginary thin film 35b of FIG. 3B exhibit a gradient of about 0.89, and thus, may be used as a mutual corresponding parameter.

Figure 7:
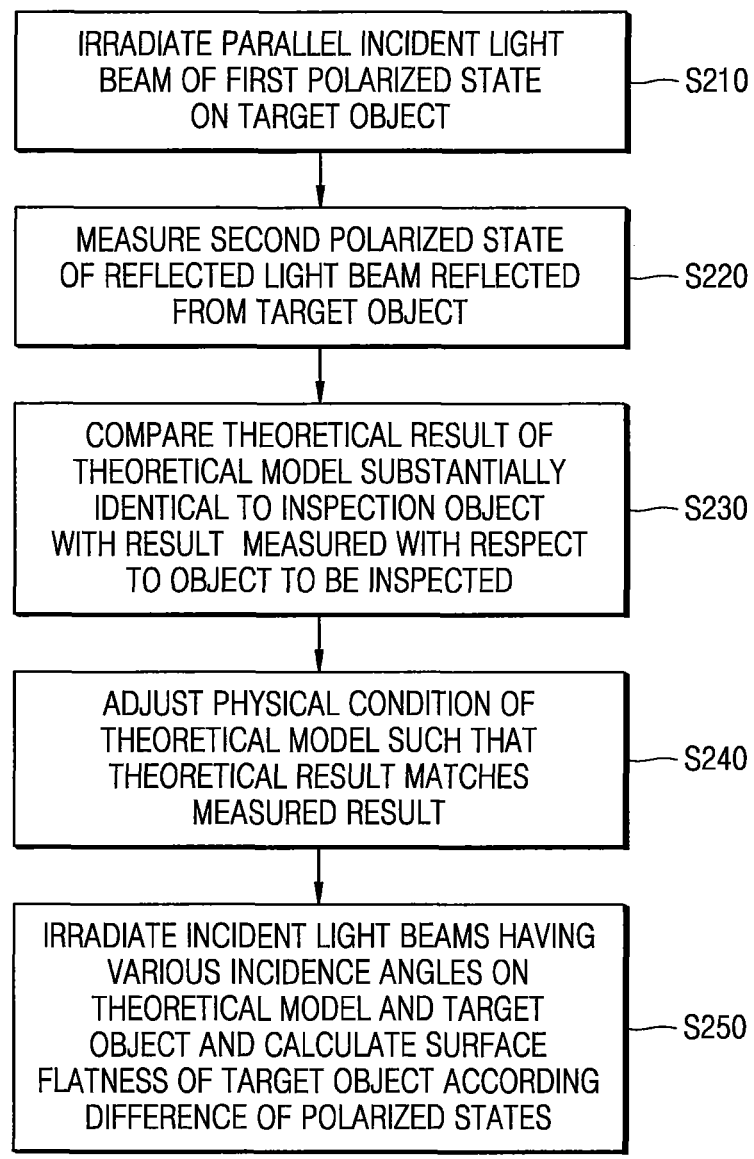
FIG. 7 is a flowchart of a surface inspecting method according to another example embodiment of the inventive concept.

FIG. 7 is a flowchart of a surface inspecting method according to another example embodiment of the inventive concept.

Referring to FIG. 7, a gradient distribution of a target object 21 may be measured from a variation in a polarization spectrum. The polarization spectrum of FIG. 3A indicates Ψ and Δ values acquired with respect to a plurality of wavelength ranges $\lambda 1, \lambda 2, \lambda 3, \ldots, \lambda n$ through the detector 29. A parallel incident light beam of a first polarized state having a cross-sectional area is irradiated on the target object 21 (S210), and a second polarized state of a reflected light beam reflected from the target object 21 may be measured (S220). After that, a theoretical model having substantially the same shape as the target object 21 is introduced, and a result of the theoretical spectrum of the theoretical model is compared with a result of a measurement spectrum of the target object 21 with respect to the polarized state (S230). The physical condition of the theoretical model may be adjusted such that the theoretical result matches the measured result (S240).

Incident light beams having various incidence angles are irradiated on the theoretical model and the target object 21, the surface flatness of the target object 21 may be calculated according a difference of the polarized states (S250). In the surface inspecting method, the inspection may be performed at a high speed because a parallel light beam is used.

Figure 8:
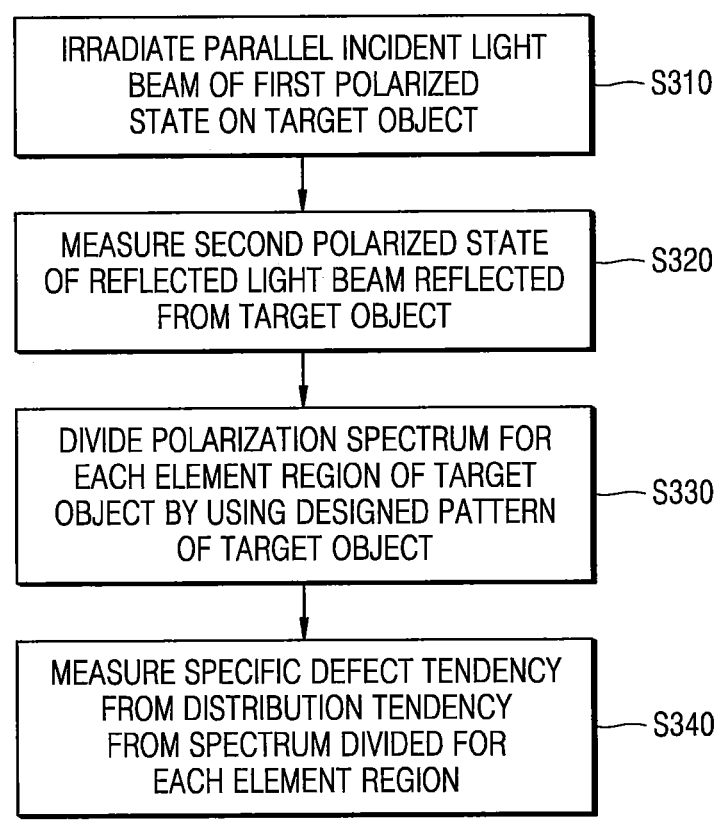
FIG. 8 is a flowchart of a surface inspecting method according to another example embodiment of the inventive concept.

FIG. 8 is a flowchart of a surface inspecting method according to another example embodiment 300 of the inventive concept.

Referring to FIG. 8, a parallel incident light beam of a first polarized state having a cross-sectional area may be irradiated on the target object 21 (S310), and a second polarized state of a reflected light beam reflected from the target object 21 may be measured (S320). After that, a polarization spectrum may be divided for each element region of the target object 21 by using a designed pattern of the target object 21 (S330). Specifically, a region may be divided for each element region and the polarization spectrum may be classified by using an initial designed pattern of the target object 21. Specific characteristics of each element region, for example, a specific defect tendency, may be measured from a distribution tendency in the spectrum classified for each element region. When the specific defect tendency for each element region is previously grasped, the influence from the manufacturing process may be previously estimated and prevented.

In this case, since the measuring of the characteristics for each element region includes a very complex calculation process, the measurement of the characteristics for each element region may be performed on the assumption that a plurality of patterns included in each element region has a central value. That is, even though characteristics of the plurality of the patterns are distributed within a predetermined range, the measurement of the characteristics for each element region may be performed on the assumption that the plurality of patterns has the central value in the predetermined range. After that, when a result with respect to the element region is measured, a fine adjustment may be performed on the plurality of patterns by setting the result as an initial value. Alternatively, a correction may be performed on the plurality of patterns by a statistical method by taking into account a variation from the central value. Due to this method, the characteristics may be more easily measured from each element region.

Figure 9:
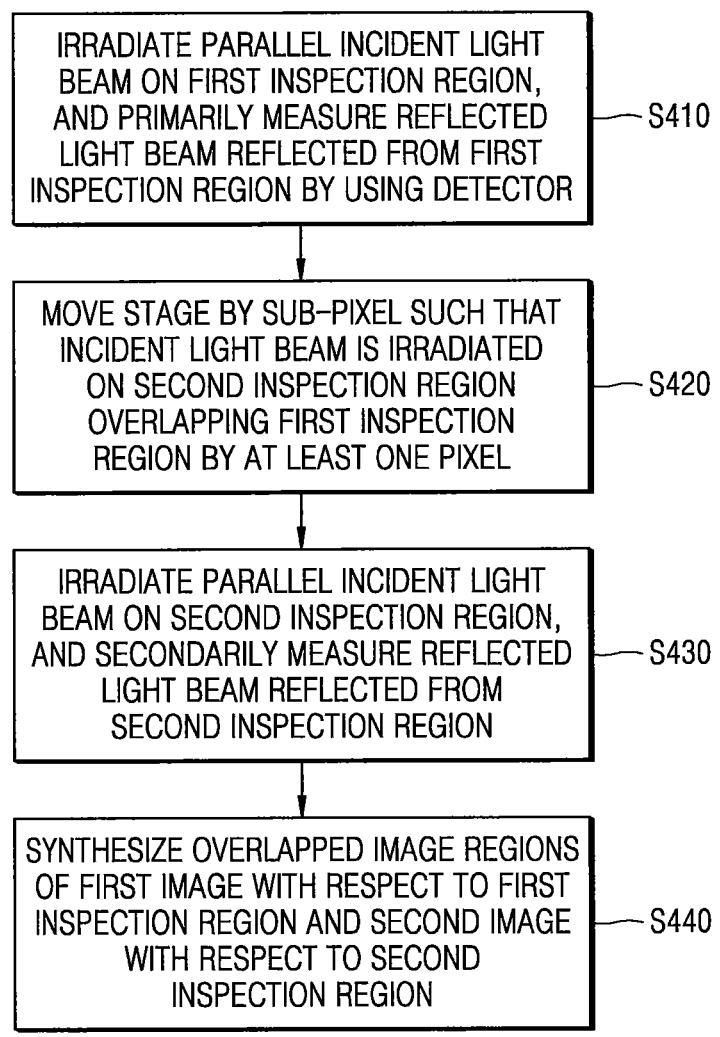
FIG. 9 is a flowchart of a surface inspecting method according to another example embodiment of the inventive concept.

FIG. 9 is a flowchart of a surface inspecting method according to another example embodiment of the inventive concept.

Referring to FIG. 9, a parallel incident light beam of a first polarized state is irradiated on a first inspection region, and a second polarized state of a reflected light beam reflected from the first inspection region is primarily measured by using the detector 29 (S410). The stage 23 supporting the target object 21 may be moved by a sub-pixel s-px such that the incident light beam is irradiated on a second inspection region overlapping the first inspection region by at least one pixel (S420). The sub-pixel s-px means that a pixel px capable of being maximally resolved by the detector 29 is divided into more smaller regions. A parallel incident light beam of a third polarized state is irradiated on the second inspection region, and a fourth polarized state of a reflected light beam reflected from the second inspection region may be secondarily measured by using the detector 29 (S430). After that, an image having a higher resolution than that of the detector 29 may be acquired by synthesizing image regions of a first image of the second polarized state with respect to the first inspection region and a second image of the third polarized state with respect to the second inspection region.

In some example embodiments, the moving operation (S420) and the second measuring operation (S430) may be repeated twice or more. In this case, an image having a higher resolution may be acquired.

Figure 10:
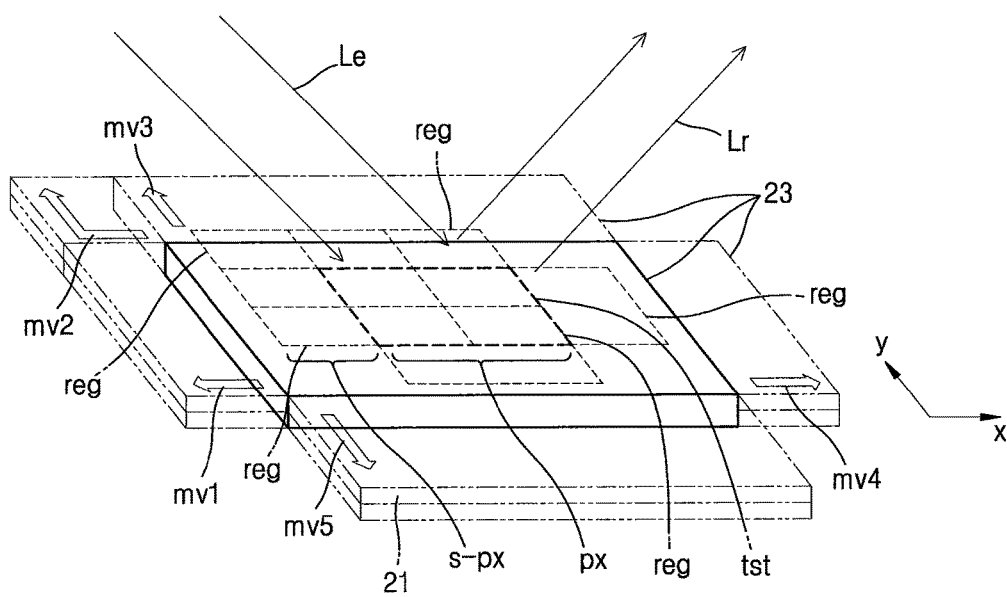
FIGS. 10 to 11 are schematic views of the surface inspecting method of FIG. 9.
Figure 11:
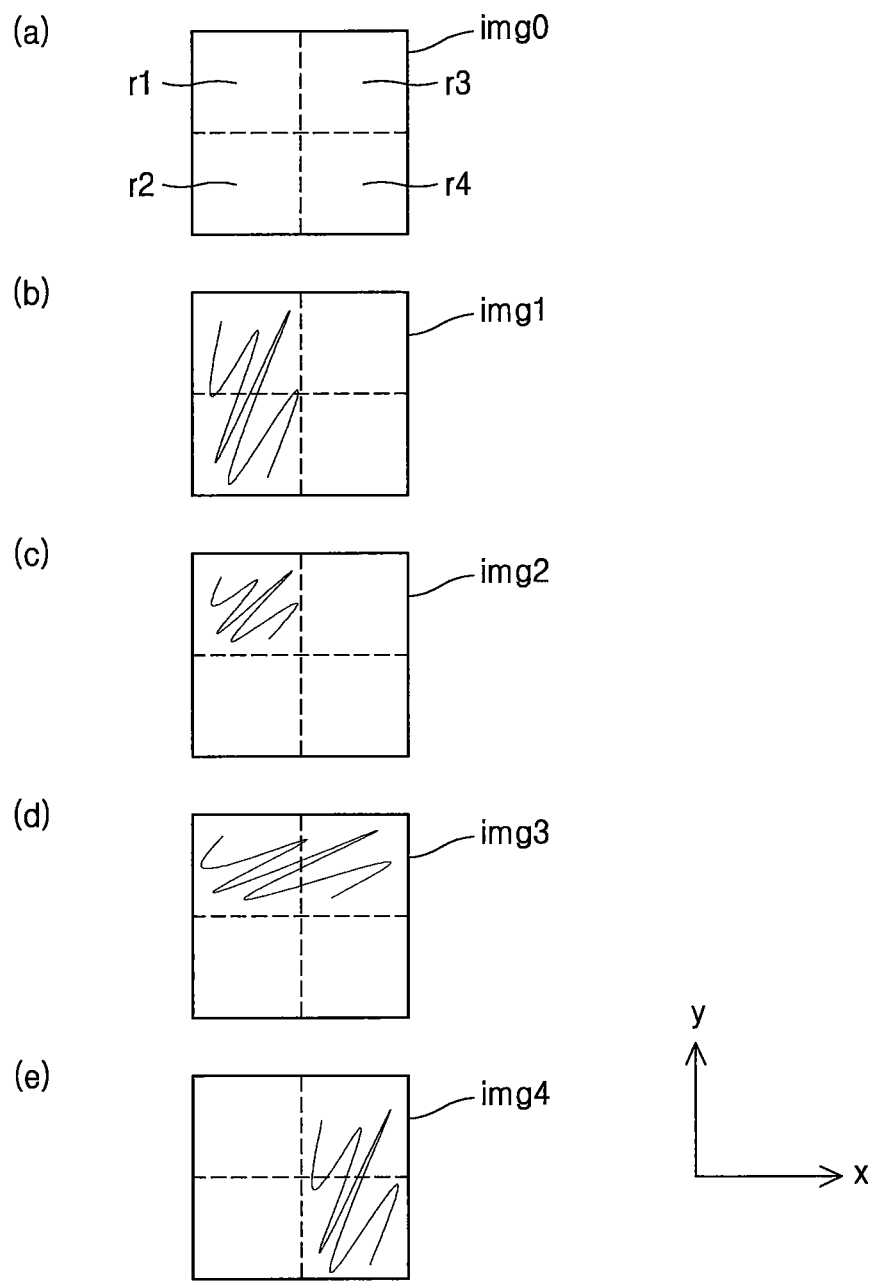

FIGS. 10 to 11 are schematic views of the surface inspecting method of FIG. 9.

Referring to FIG. 10, the target object 21 may be moved toward a region to be measured by moving the stage 23 in an X direction and/or a Y direction. At this time, the stage 23 may be moved by a sub-pixel s-px of the detector 29 of FIG. 1. The sub-pixel s-px means that a pixel px capable of being maximally resolved by the detector 29 is divided into more smaller regions. Therefore, after the stage 23 on which the target object 21 is disposed, is moved by the sub-pixel s-px, image information acquired by the detector 29 of FIG. 1 includes a region overlapping, by an area of at least one sub-pixel s-px, image information acquired before the stage 23 is moved. Image information, which has a higher resolution than an original resolution of the detector 29 of FIG. 1, may be acquired.

Specifically, a reference region reg, which indicates a specific location of the target object 21, is marked on the target object 21 disposed on the stage 23. The reference region reg is a region having the same area as one pixel px. Before the stage 23 is moved, the reference region reg is included in an inspection region tst on which the light beam Le is irradiated. Therefore, the light beam Le may be irradiated on the reference region reg, and initial image information of the reference region reg may be acquired by the reflected light beam Lr reflected from the reference region reg. Referring to FIG. 11, the initial image information img0, which is acquired by capturing the reference region reg before the stage 23 is moved, includes first, second, third, and fourth regions r1, r2, r3, and r4. However, the reference region reg has a region having the same areas as one pixel px, and the initial image information img0 itself may not distinguish the first, second, third, and fourth regions r1, r2, r3, and r4 in the reference region reg.

The stage 23 may be moved in the X-direction and/or the Y-direction by one sub-pixel s-px with respect to the reference region reg. The stage 23 may be moved in the X-direction by the sub-pixel s-px (first movement mv1). After the first movement mv1, a right half of the reference region reg of the target object 21 overlaps the inspection region tst by two sub-pixels s-px. Therefore, after the first movement mv1, a region including a right region of the reference region reg and a left region of the reference region reg appears in the inspection region tst, and first image information img1 partially overlapping the initial image information img0 is acquired. Referring to FIG. 11, the first image information img1 is acquired by capturing the inspection region tst after the first movement mv1. Therefore, the right half of the reference region reg appears on the left half of the first image information img1. That is, the left half of the first image information img1 may be captured while overlapping the third and fourth regions r3 and r4 of the reference region reg. As described above, if the inspection region tst is captured after second, third, and fourth movements mv2, mv3, and mv4, second image information img2, third image information img3, and fourth image information img4 may be captured while overlapping the first region r1, the first and third regions r1 and r3, and the third and fourth regions r3 and r4, respectively. The plurality of pieces of image information img0, img1, img2, img3, and img4 may be output as single final image information by synthesizing overlapped portions. The plurality of pieces of image information synthesized in the first, second, third, and fourth regions r1, r2, r3, and r4 are different from one another. Thus, although the reference region reg has the same range as one pixel px of the detector 29 of FIG. 1, the final image information, which has the same resolution and spatial resolution as the sub-pixel s-px capable of distinguishing the first, second, third, and fourth regions r1, r2, r3, and r4, may be acquired.

FIG. 10 illustrates that the stage 23 is moved in vertical and horizontal directions with respect to the reference region reg, but the inventive concept is not limited thereto. In some example embodiments, the stage 23 may be moved in the X direction and/or the Y-direction by integer times of the width of the sub-pixel s-px and may be continuously moved in the X direction or the Y-direction.

FIG. 10 illustrates that image information with respect to the pixel px is acquired through four sub-pixel s-px, but the inventive concept is not limited thereto. Since the pixel may have at least two sub-pixels s-px, the number of sub-pixels included in the pixel px may be two, three, or five or more.

While the inventive concept has been particularly shown and described with reference to example embodiments thereof, it will be understood that various changes in form and details may be made therein without departing from the spirit and scope of the following claims.

What is claimed is:

1. A surface inspecting method comprising:
    irradiating an incident light beam of a first polarized state on a target object, the incident light beam comprising parallel light and having a cross-sectional area:
    measuring a second polarized state of a reflected light beam reflected from the target object; and
    performing an inspection on an entire area of the target object on which the incident light beam is irradiated, based on a variation between the first polarized state and the second polarized state, wherein the measuring is performed by a detector, and a sub-pixel means that a pixel region capable of being maximally resolved by the detector is divided into at least two regions, and
    the surface inspecting method further comprises, after the inspection, moving a stage supporting the target object by the sub-pixel.

2. The surface inspecting method of claim 1, wherein the measuring of the second polarized state comprises:
    irradiating a plurality of light beams having different wavelength ranges on the target object in time series; and
    measuring a plurality of light beams reflected from the target object in time series.

3. The surface inspecting method of claim 1, wherein the surface inspecting method is performed with respect to each of a plurality of wavelength ranges, and
    the surface inspecting method further comprises outputting, in an image form, a polarization spectrum indicating each second polarized state according to the plurality of wavelength ranges after the inspection.

4. The surface inspecting method of claim 1, wherein the performing of the inspection comprises:
    providing a theoretical model having substantially a same shape as the target object and comparing a theoretical result of the theoretical model with respect to a polarized state and a result measured with respect to the target object;
    adjusting a parameter of the theoretical model such that the theoretical result matches the measured result; and
    irradiating incident light beams having various incidence angles on the theoretical model and the target object and calculating the flatness of the surface of the target object according to a difference between polarized states of reflected light beams reflected from the theoretical model and the target object.

5. The surface inspecting method of claim 1, wherein the performing of the inspection comprises:
    dividing a polarization spectrum for each element region with respect to the target object by using a designed pattern of the target object; and
    measuring a specific defect tendency for each element region from a distribution tendency of the polarization spectrum divided for each element region.

6. The surface inspecting method of claim 1, wherein the target object comprises a pattern, and
    the performing of the inspection comprises:
    calculating physical quantities of an imaginary thin film indicating a same polarized state as the second polarized state with respect to the incident light beam; and
    calculating physical quantities of the target object from the physical quantities of the imaginary thin film by using a relationship in which a height of the pattern is proportional to a thickness of the imaginary thin film and a width of the pattern is proportional to a value acquired by dividing a materials mixing ratio of the imaginary thin film by the height of the pattern.

7. The surface inspecting method of claim 6, wherein the target object comprises a plurality of patterns that are periodically formed.

8. The surface inspecting method of claim 6, wherein the calculating of the physical quantities of the imaginary thin film comprises:
    providing a theoretical model having substantially a same shape as the imaginary thin film and comparing a theoretical result of the theoretical model with a result measured with respect to the target object;
    adjusting a parameter of the theoretical model and acquiring a condition in which the theoretical result matches the measured result; and
    calculating the physical quantities of the imaginary thin film using the condition.

9. The surface inspecting method of claim 8, further comprising outputting, in an image form, a difference between a theoretical spectrum indicating a theoretical result with respect to a plurality of wavelength ranges of the theoretical model and a measurement spectrum indicting a result measured with respect to the plurality of wavelength ranges in the target object; and
    detecting defects of the target object.

10. A surface inspecting method comprising:
    irradiating an incident light beam of a first polarized state on a first inspection region, and primarily measuring a second polarized state of a reflected light beam reflected from the first inspection region with a detector;
    moving a stage supporting a target object by a sub-pixel such that the incident light beam is irradiated on a second inspection region overlapping the first inspection region by an area of at least one sub-pixel; and
    irradiating an incident light beam of a third polarized state on the second inspection region, and secondarily measuring a fourth polarized state of a reflected light beam reflected from the second inspection region with the detector, wherein a sub-pixel is smaller than a pixel region, and the pixel region is a region that is capable of being maximally resolved by the detector.

11. The surface inspecting method of claim 10, wherein the incident light beam is a parallel light beam having a cross-sectional area, and
the incident light beam is irradiated on the entire first inspection region in the primarily measuring and is irradiated on the entire second inspection region in the secondarily measuring.

12. The surface inspecting method of claim 10, further comprising synthesizing overlapped regions of a first image of the second polarized state with respect to the first inspection region and a second image of the third polarized state with respect to the second inspection region.

13. The surface inspecting method of claim 10, wherein the moving and the secondarily measuring are repeated twice or more.

14. The surface inspecting method of claim 10, wherein the stage is movable in at least one of a vertical direction and a horizontal direction by at least one sub-pixel.

15. A surface inspecting method comprising:
irradiating an incident light beam of a first polarized state on a first inspection region, and primarily measuring a second polarized state of a reflected light beam reflected from the first inspection region with a detector; and
irradiating an incident light beam of a third polarized state on a second inspection region, and secondarily measuring a fourth polarized state of a reflected light beam reflected from the second inspection region with the detector,
wherein the secon4 inspection region is offset from the first inspection region by less than a pixel of the detector, and the pixel of the detector is a region that is capable of being maximally resolved by the detector.

16. The surface inspecting method of claim 15, wherein the incident light beam is a parallel light beam having a cross-sectional area, and
the incident light beam is irradiated on the entire first inspection region in the primarily measuring and is irradiated on the entire second inspection region in the secondarily measuring.

17. The surface inspecting method of claim 15, further comprising synthesizing overlapped regions of a first image of the second polarized state with respect to the first inspection region and a second image of the third polarized state with respect to the second inspection region.

18. The surface inspecting method of claim 15, wherein the first and second inspection regions are offset by moving a stage supporting a target object by a sub-pixel such that the incident light beam is irradiated on a second inspection region overlapping the first inspection region by an area of at least one sub-pixel.

19. The surface inspecting method of claim 18, further comprising repeating the moving and the secondarily measuring steps.

* * * * *